United States Patent
Lilley et al.

(10) Patent No.: US 9,170,189 B2
(45) Date of Patent: Oct. 27, 2015

(54) BOND STRENGTH TESTER WITH SWITCHABLE BACKLASH CONTROL

(71) Applicant: Nordson Corporation, Westlake, OH (US)

(72) Inventors: David Lilley, Colchester (GB); Martin Bugg, Ipswich (GB); Robert John Sykes, Tendring (GB)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 14/224,560

(22) Filed: Mar. 25, 2014

(65) Prior Publication Data

US 2014/0190269 A1  Jul. 10, 2014

Related U.S. Application Data

(63) Continuation of application No. 13/034,260, filed on Feb. 24, 2011, now Pat. No. 8,714,025.

(30) Foreign Application Priority Data

Mar. 5, 2010 (EP) ..................................... 10002333

(51) Int. Cl.
- *G01N 21/00* (2006.01)
- *G01N 19/04* (2006.01)
- *G01N 3/24* (2006.01)

(52) U.S. Cl.
CPC ................. *G01N 19/04* (2013.01); *G01N 3/24* (2013.01); *G01N 2203/0025* (2013.01); *G01N 2203/0623* (2013.01); *H01L 2224/859* (2013.01)

(58) Field of Classification Search
CPC ..................................................... G01N 21/00

USPC ............................................................ 73/788
See application file for complete search history.

(56) References Cited

U.S. PATENT DOCUMENTS

| | | | |
|---|---|---|---|
| 2,280,760 | A | 4/1942 | Martellotti |
| 3,101,610 | A | 8/1963 | Rosander |

(Continued)

FOREIGN PATENT DOCUMENTS

| | | |
|---|---|---|
| CN | 1425861 A | 6/2003 |
| CN | 1998075 | 7/2007 |

(Continued)

OTHER PUBLICATIONS

European Patent Office, European Search Report in EP Application No. 10002333, Jul. 29, 2010.

(Continued)

*Primary Examiner* — Lisa Caputo
*Assistant Examiner* — Jamel Williams
(74) *Attorney, Agent, or Firm* — Wood, Herron & Evans, LLP

(57) ABSTRACT

A testing apparatus for testing the strength of a material connection to a substrate. A drive mechanism couples a test tool mount to a main body and allows for relative movement between the test tool mount and the main body in an axial direction. A biasing element is coupled between the main body and the test tool mount, that, in operation, biases the test tool mount relative to the main body in an axial direction. The biasing element is switchable between a first state in which the test tool mount is biased either toward or away from the substrate and another state in which the biasing element provides one of: no biasing force to the test tool mount toward or away from the substrate, or a biasing force in a direction opposite to the direction of bias applied in the first state.

13 Claims, 11 Drawing Sheets

(56) References Cited

U.S. PATENT DOCUMENTS

| | | | |
|---|---|---|---|
| 3,289,357 A | 12/1966 | Decker | |
| 3,580,065 A | 5/1971 | Strittmater et al. | |
| 3,945,248 A | 3/1976 | West | |
| 4,312,212 A | 1/1982 | Clendenin | |
| 4,893,513 A * | 1/1990 | Schroeder et al. | 73/827 |
| 5,892,157 A * | 4/1999 | Syre | 73/812 |
| 6,078,387 A * | 6/2000 | Sykes | 356/244 |
| 6,301,971 B1 | 10/2001 | Sykes | |
| 6,564,115 B1 * | 5/2003 | Kinnaird | 700/121 |
| 7,735,711 B2 * | 6/2010 | Farassat | 228/103 |
| 7,748,278 B2 | 7/2010 | Sykes | |
| 7,810,374 B2 * | 10/2010 | Zhang et al. | 73/12.09 |
| 7,950,290 B2 | 5/2011 | Sykes | |
| 8,015,883 B2 | 9/2011 | Peecock et al. | |
| 8,100,021 B2 * | 1/2012 | Sykes | 73/827 |
| 8,424,390 B2 | 4/2013 | Lilley et al. | |
| 2008/0190212 A1 * | 8/2008 | Sykes | 73/841 |

FOREIGN PATENT DOCUMENTS

| | | |
|---|---|---|
| CN | 201031936 Y | 3/2008 |
| CN | 101258309 A | 9/2008 |
| JP | 5027354 | 8/1975 |
| JP | 54115289 | 9/1979 |
| JP | 2005265806 A | 9/2005 |

OTHER PUBLICATIONS

The State Intellectual Property Office of the People's Republic of China, Office Action in CN Application No. 201110053931.4, Jan. 21, 2014.

The State Intellectual Property Office of the People's Republic of China, Second Office Action in CN Application No. 201110053931.4, Sep. 19, 2014.

Japanese Patent Office, Office Action in JP Application No. 2011-47820, Oct. 20, 2014.

Intellectual Property Office, Office Action and Search Report in Taiwan Application No. 100106546, Mar. 10, 2015.

* cited by examiner

BOND STRENGTH TESTER WITH SWITCHABLE BACKLASH CONTROL

CROSS-REFERENCE TO RELATED APPLICATIONS

This application is a continuation of U.S. application Ser. No. 13/034,260, filed Feb. 24, 2011 (pending), which claims the priority of EP Application No. 10002333.2, filed Mar. 5, 2010, the disclosures of which are incorporated by reference herein.

FIELD OF THE INVENTION

The present invention relates to a device for testing the strength of electrical bonds on semiconductor devices. In particular, the invention relates to a device that is able to perform different types of tests such as a shear test, a pull test and a push test on electrical bonds.

BACKGROUND TO THE INVENTION

Semiconductor devices are very small, typically from 5 mm×5 mm square to 50 mm×50 mm square, and typically comprise numerous sites for the bonding of electrical conductors to a semiconductor substrate. Each bond consists of a solder or gold ball deposit adhered to the substrate. Very thin wires, usually about 0.025 mm in diameter, may be embedded in the ball deposits.

It is necessary to test the bond strength of the bonds, in order to be confident that a particular bonding method is adequate. Because of the very small size of the bonds, tools used to test the bond strength of these bonds must be able to measure very small forces and deflections accurately.

There are several different types of bond tests that are used to test bond strength. For example, shear testing tests the shear strength of a bond by applying a shear force to the side of the bond and shearing the bond off the substrate. Pull testing tests the pull strength of the bond by pulling a wire embedded in a ball deposit away from the substrate. In a push test, a force, or load, is applied in the vertical plane directly downward onto a bond.

Machines that perform these tests typically comprise a bond test tool, be it a shear test tool, push test tool or a pull test tool, that can be positioned relative to the bond under test and then either the bond or the tool are moved in order to perform the test by measuring the force needed to break the bond.

As mentioned above, in these tests it is necessary to be able to measure very small forces and deflections. Positioning of a test tool is typically achieved using some form of screw and nut rotational drive assembly. For example, a test tool may be mounted to an assembly of components that includes a nut which moves along a threaded screw when the threaded screw is driven by a servo motor. This mechanism may be used for positioning the tool correctly prior to a shear, push or pull test and may be used to drive the test tool during a pull test.

When using a screw and nut arrangement for providing the movement of the test tool towards and away from the substrate, inevitable clearances must be provided between the mating components of the screw and nut to prevent jamming, allow for thermal expansion and manufacturing variances, etc. This clearance is referred to as "backlash". This clearance limits the accuracy to which the test tool can be initially positioned and to which the desired position of a test tool can be accurately maintained during a bond strength test.

In prior art bond testing machines, wherein the test tool is driven up and down along the vertical axis by a screw and nut drive mechanism, a spring in tension has been positioned above the tool and used to bias the tool upwardly to close the clearance between the upper thread surfaces of the nut and the thread surfaces of the screw. This has reduced backlash when the tool is used for shear testing or push testing, because these tests cause an upward force to be applied by the tool during the test. For example, in shear testing, as the test tool shears a ball deposit off the substrate, a vertical force component results, causing the ball deposit to push up on the tool. Since the tool is already being biased in the upward position by the spring, the backlash clearance has already been closed, and thus, the shear or push test itself does not cause a tool position problem associated with backlash.

However, the use of a biasing spring has not completely eliminated the backlash problem during shear and push tests because the force applied by the spring, which as mentioned is in tension, changes as the spring is stretched. The more the spring is stretched, the greater the biasing force it applies. Therefore, a varying force is applied by the spring over the range of travel of the nut along the screw. Consequently, the spring applies more force to reduce backlash clearance when the spring has been stretched to the lower end of travel of the nut along the screw than it does when the spring is stretched to a lesser extent at the upper end of travel of the nut along the screw. Thus, the use of the spring has reduced backlash problems in shear and push tests, but it has not eliminated backlash problems.

In addition, in shear testing, it is very important that the lower end of the test tool maintain a very small, closely controlled standoff distance from the substrate. In that the upward bias of the spring varies depending on the length of the spring, the ability of the upward bias force to close off clearances also varies, making it difficult to accurately and reliably control the standoff distance for every position of the test tool above the substrate.

In a pull testing, moreover, a more significant backlash problem exists which is not solved by the use of the spring. In a pull test, the test tool is in the shape of the hook and it hooks under a wire that is bonded to a substrate. The test tool pulls up on the wire to pull the wire off a bond on the substrate and the force required to break that bond is measured. Typically the wire has been bonded to a solder ball on the substrate. As the wire is pulled, it exerts a downward force on the test tool. This downward force is pulling the tool down against the force of the spring. At some point, this force can overcome the spring force and cause the nut to move downward away from contact between its upper threaded surfaces and the screw until it makes contact with its lower threaded surfaces and the screw, closing the backlash clearance between the lower threaded surfaces of the nut and the threads of the screw. This movement to close the backlash clearance below the nut distorts the signals provided by the strain gauges, or other transducers, that are later described, and causes inaccurate force readings.

Furthermore, in the case of shear, push and pull tests, it is desirable that the nut and screw remain engaged in contact in a constant fashion to accurately control the axial movement of the test tool in a repeatable way. This has not always been achievable with the spring solution of the prior art.

SUMMARY OF THE INVENTION

The present invention is defined in the appended independent claims to which reference should be made. Preferred features are defined in the dependent claims.

To solve the aforementioned problems of the prior art spring solution, in the preferred embodiment of the present invention, a backlash control element is used to apply a constant biasing force to the nut that travels along the drive screw in a bond testing machine, which can be used for shear testing, push testing or pull testing.

The backlash control element can be in the form of a pneumatic piston and cylinder, with the cylinder fixed in position relative to the drive screw, and the piston fixed for movement with the nut that travels along the drive screw. This solution allows a desired bias force to be set, by setting the pressure in the cylinder, and then maintained regardless of the position of the nut along the drive screw. Thus, unlike the spring solution of the prior art, the biasing force applied to the nut can be specifically selected, and once selected, can be maintained constant as the nut moves along the length of the screw.

By providing a constant bias to the nut in both axial directions along the screw, the positional accuracy of the test tool relative to the substrate is improved relative to the prior art. This improvement in positional accuracy increases the reliability and repeatability of the force measurements made by the bond testing device.

A backlash control element in the form, for example, of a piston and cylinder, can also be used in such a way that bias is applied to the nut in the upward direction by the piston during shear and push tests, but no bias is applied during pull testing by venting the air pressure from the cylinder so that the piston can move freely. When the pressure is vented, instead of applying a bias by means of the piston and cylinder, the weight of the moving components themselves is relied upon to provide adequate bias to close the backlash clearance. This was not possible with the prior art spring solution in that the spring was always active to support at least part of the weight of the moving components of the system because the spring bias could not be removed during pull tests.

A backlash control element in the form, for example, of a piston and cylinder, can also be used to augment the drive force supplied by the screw and nut drive mechanism. For example, if the machine is used for a pull test, the screw drive will exert a given amount of upward force on the nut and test tool. If the piston is biased in the upward direction against the nut, the force of the piston will then be added to the drive force of the screw to produce a greater total upward force on the bond. Likewise, if the machine is used for push test, the screw drive will exert an amount of downward force on the nut and test tool. If the piston is biased in the downward direction against the nut, the force of the piston will be added to the drive force of the screw to produce a greater total downward force on the bond.

Consequently, in one aspect, the invention provides a bond testing apparatus comprising a main body, a test tool mount for holding a bond test tool, an axial drive mechanism, preferably comprising a screw and nut assembly, the drive mechanism coupling the test tool mount to the main body and allowing for relative movement between the test tool mount and the main body in an axial direction, and a backlash control element, coupled to the main body and the test tool mount, that, in operation, biases the test tool mount relative to the main body in an axial direction, wherein the backlash control element is switchable between a first state in which the test tool mount is biased in a first axial direction and a second state in which the test tool is biased in a second axial direction or in which the backlash control element provides no biasing force in the axial direction.

Preferably, the backlash control element comprises a pneumatically operated piston and cylinder.

Preferably, the force applied by the backlash control element can be set at a desired level, but once the force has been set, that force can be maintained at a constant level regardless of the axial position of the test tool, to improve the reliability and repeatability of bond tests.

Preferably, the backlash control element comprises a coupling between the moving portions of the apparatus and the non-moving portions of the apparatus, and most preferably, comprises an element that supports the nut in a screw and nut drive mechanism.

Preferably, the backlash control element comprises a pneumatically operated piston and cylinder which applies an upward biasing force during a shear test or push test, and a downward biasing force, or no biasing force, during a pull test.

Preferably, the apparatus further comprises a controller connected to a user interface, the controller and user interface being configured to allow a user to select a type of bond test, and wherein the controller is connected to the backlash control element and controls switching of the backlash control element between the first state and the second state in dependence on the type of bond test selected.

In another aspect, the invention provides a method of testing the bond strength of a bond on a substrate by either a shear test or a pull test, using a bond testing device comprising a test tool that is coupled to a main body by a coupling, comprising the steps of: selecting either a shear test or a pull test; and if a shear test is selected, applying a biasing force on the test tool in a first direction to remove backlash from the coupling; positioning the test tool relative to the bond; providing relative movement between the test tool and the substrate to shear the bond off the substrate; and recording the force applied to the test tool by the bond.

Preferably, the method further comprises the step of applying a biasing force on the test tool in a second direction to remove backlash from the coupling, if a pull test is selected.

Preferably, the step of applying a biasing force comprises operating a pneumatic cylinder and piston coupled between the test tool and the main body.

Preferably, the first direction is an upward direction and the second direction is a downward direction.

Preferably, the method further comprises the step of initially positioning the test tool relative to the bond prior to applying a biasing force on the test tool, and more accurately positioning the test tool relative to the bond subsequent to applying a biasing force on the test tool.

The arrangement of the present invention allows a test tool to perform shear tests and pull tests, in which backlash is substantially eliminated. It allows pull and shear tests to be performed by the same apparatus, with good positional accuracy.

BRIEF DESCRIPTION OF THE DRAWINGS

Embodiments of the present invention will now be described in detail, by way of example only, with reference to the accompanying drawings, in which.

DETAILED DESCRIPTION

Figure 1A:
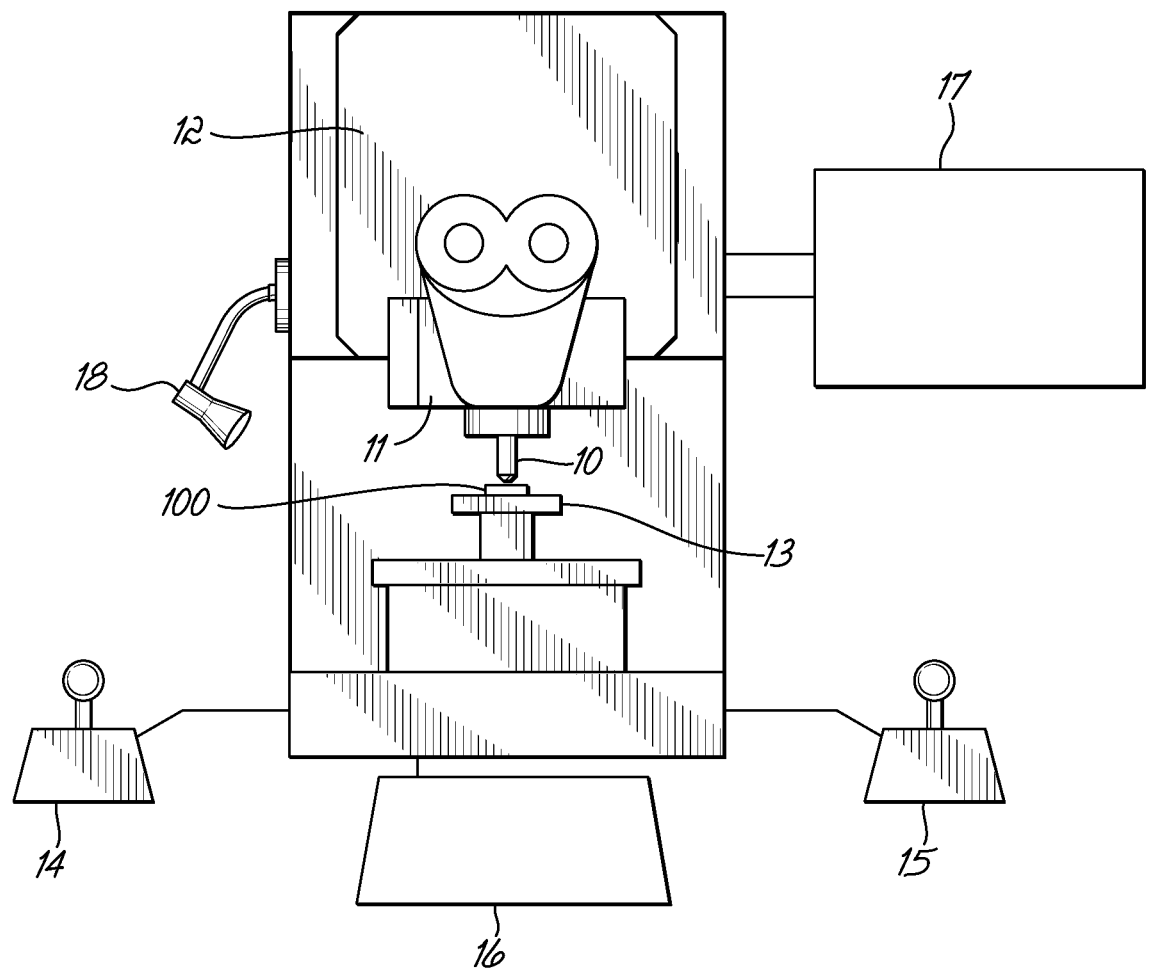
FIG. 1A is a front view of a test apparatus in accordance with the present invention.

FIG. 1A is an illustration of a bond testing device in accordance with the present invention. The device comprises a test tool 10 mounted to a cartridge 11, which is itself mounted to the main body of the device 12. Beneath the test tool is a motorized stage table 13, on which samples, or substrates 100, to be tested can be mounted.

The test tool 10, mounted to cartridge 11, can be a shear tool, push tool or a pull tool and can be switched in order to perform different tests. An example of a suitable shear tool is described in U.S. Pat. No. 6,078,387, the contents of which are incorporated herein by reference. An example of a suitable pull tool is described in U.S. Pat. No. 6,301,971, the contents of which are incorporated herein by reference.

Figure 1B:
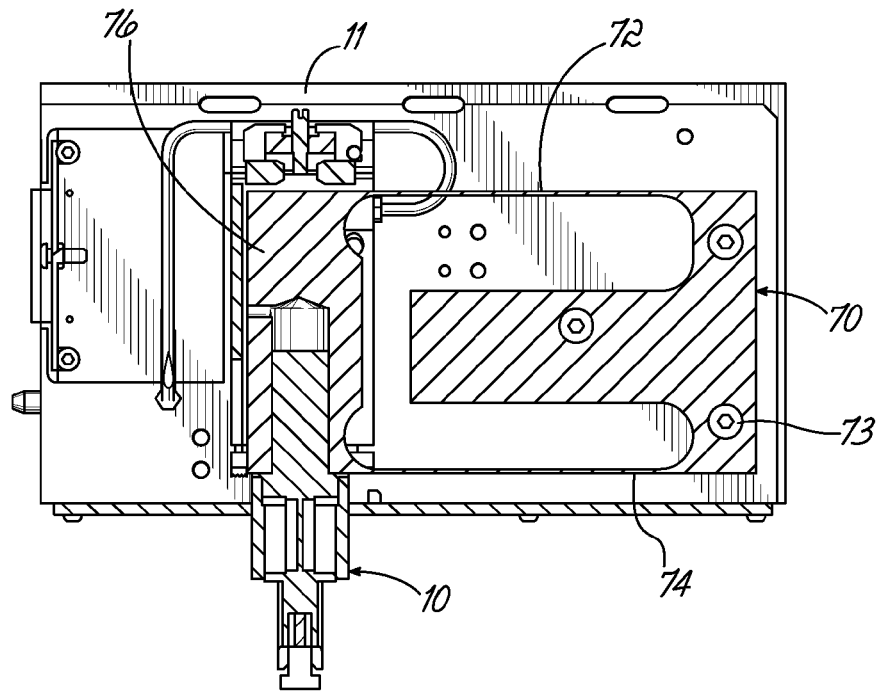
FIG. 1B is a cross-sectional view showing the test tool supported by the tool mounting bracket.
Figure 1C:
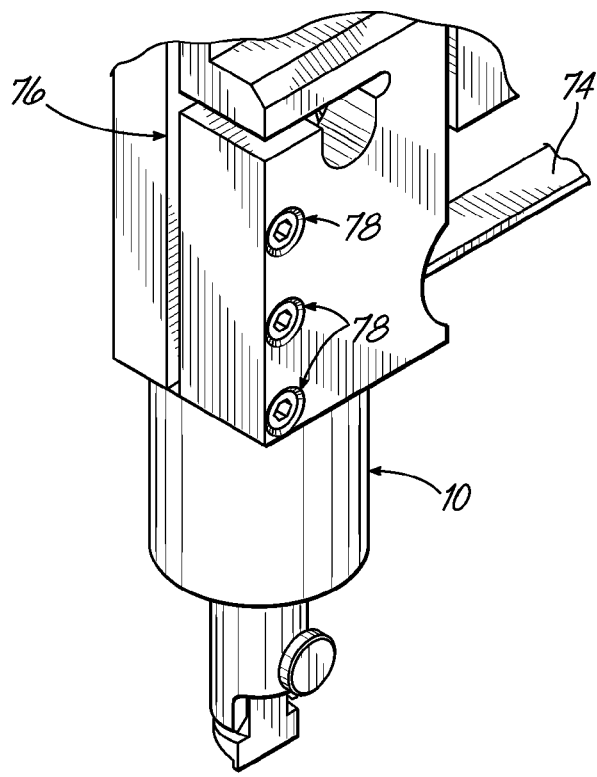
FIG. 1C is a perspective view showing the test tool clamped to the tool mounting bracket.
Figure 2A:
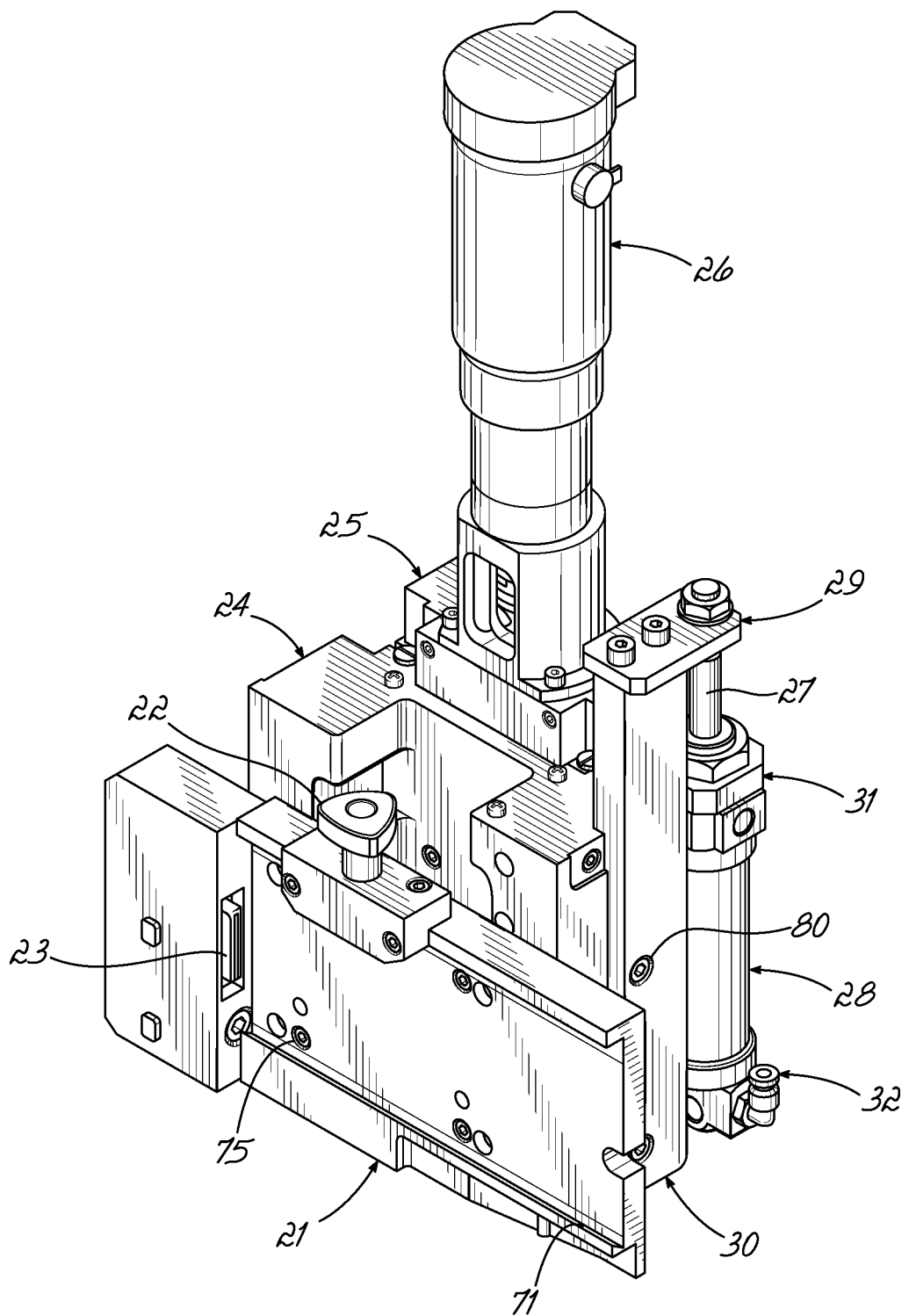
FIG. 2A is a perspective view of a test tool mount and drive, including an anti backlash cylinder in accordance with the present invention.

As shown in FIG. 1B, the test tool 10 is typically attached to the cartridge 11 by a tool mount bracket 70 having cantilever arms 72, 74 fixed at one end to the cartridge 11 by screws 73, with the free ends of the arms 72, 74 supporting a clamp 76. As shown in FIG. 1C, the tool 10 is clamped in clamp 76 by means of clamp screw 78. FIG. 2A shows the retaining channel 71 on the cartridge mount plate 21 into which the cartridge 11 is slid and then secured using one or more screws 22. The cartridge mount plate 21 includes a data port 23 that couples with an electrical connector on the cartridge 11 for transferring data from the transducers (later described) of cartridge 11 to a PC. A cartridge and test tool assembly of this type is well known in the prior art. See for example the Dage 4000 multipurpose bond tester available from Dage Holdings Limited, 25 Faraday Road, Rabans Lane Industrial Area, Aylesbury, Buckinghamshire, United Kingdom. However, any suitable means for attaching a test tool to the cartridge mount plate may be used in a system in accordance with the present invention.

The cartridge 11 is moveable in a direction normal to the surface of the substrate 100 on the stage table 13. This allows the test tool 10 to be positioned relative to the substrate 100 under test so that it will contact a particular bond during a test. Relative movement between the test tool 10 and the table 13 in a direction parallel to the plane of the substrate 100 is typically achieved by moving the table 13. Movement of the table 13 is achieved using suitable servo motors or stepper motors, coupled to the table 13 via a lead screw and nut, ball screw and nut, or suitable belt-drive mechanism (not shown), as is also well known in the prior art, such as the Dage 4000 Multipurpose Bond Tester referenced above Also shown in FIG. 1A are control devices, comprising two joystick controls 14, 15 to allow for controlling movement of the table 13, and a keyboard 16. A display 17, a light 18 for illuminating the substrate 100 under test, and a microscope, aiding accurate positioning of the test tool 10, are also shown. These features are also all well known in the prior art, such as the Dage 4000 Multipurpose Bond Tester referenced above.

FIG. 2A shows the mounting plate 21 and its connection to the main body 25. As has been described, the test tool (not shown in FIG. 2A) must be moveable towards and away from a substrate under test. This is achieved by moving the cartridge mount plate 21, to which the test tool 10 is attached, relative to the main body 25 of the device in a direction towards and away from the substrate, herein referred to as the z-axis direction or axial direction. The cartridge mount plate 21 is rigidly coupled to a moving block 24, using screws 75. The moving block 24 is coupled to the main body 25 via a ball screw (or lead screw) 33 and nut 34 and nut block 35 that is driven by a servo motor or stepper motor 26. This is described in more detail below with reference to FIG. 4.

As described above, the use of a screw and nut arrangement for providing the movement of the test tool 10 towards and away from the substrate 100 leads to the problem of backlash in the mechanism.

Figure 2B:
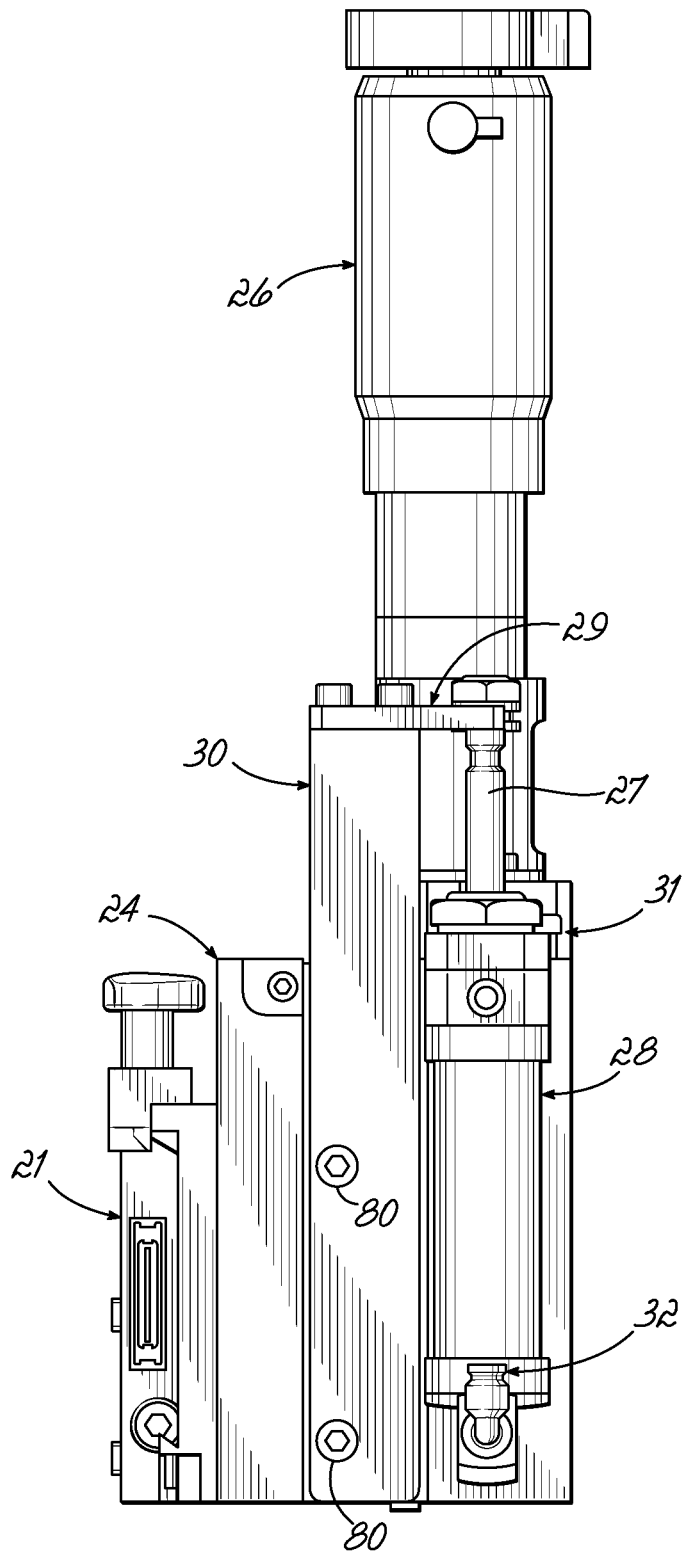
FIG. 2B is a side view of the assembly of FIG. 2A.
Figure 2C:
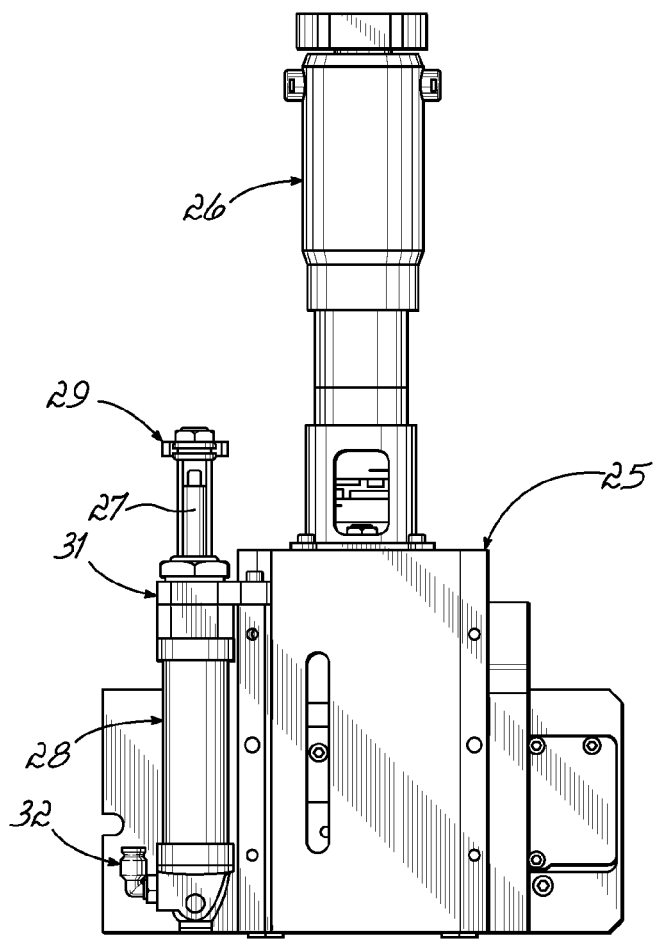
FIG. 2C is a rear view of the assembly of FIG. 2A.
Figure 2D:
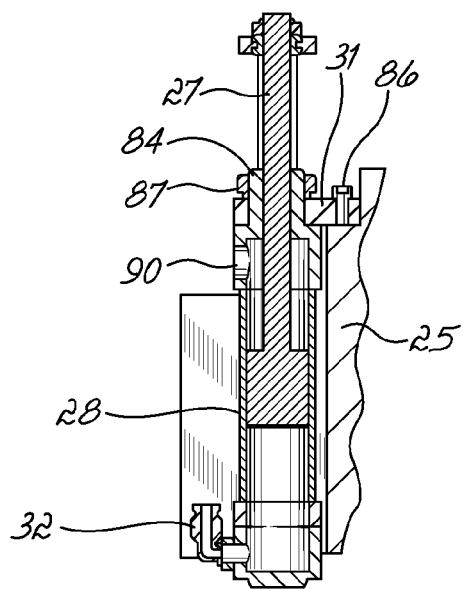
FIG. 2D is a cross-sectional view of an alternative embodiment of the anti backlash cylinder in accordance with the present invention.

In order to remove the problem of backlash, an anti-backlash mechanism is included. This mechanism is shown in FIGS. 2A-2C and 4, and preferably comprises a pneumatic piston 27 and cylinder 28. The piston 27 is coupled to the vertically movable components of the system which mainly comprise the coupling plate 29, coupling block 30, moving block 24, mounting plate 21 (and cartridge 11 and test tool 10), nut block 35 and nut 34. While only the shaft portion of the piston 27 is shown in FIGS. 2A-2C, piston 27 also includes a piston head portion at its lower end as shown in FIG. 2D. The cylinder 28 is connected to the components of the system which do not move vertically. These components comprise the cylinder mount plate 31 (later described), main body 25 and the components driving the screw 33. As will be described in more detail below the piston 27 is coupled for movement with the moving block, or nut block, 35 which supports nut 34, and the cylinder 28 is fixed in position relative to the screw 33 of the vertical axis drive mechanism. In this way, the pneumatically driven piston 27 is able to apply a controllable biasing force to the nut 34 so that backlash is removed from the system. The biasing force can also be switched off.

FIG. 2B is a side view of the arrangement of FIG. 2A, showing the connection of the piston 27 to the moving block 24, via the coupling plate 29 and coupling block 30, which is bolted by bolts 80 to the moving block 24

FIG. 2C is a rear view of the assembly of FIG. 2A, showing the connection of the cylinder 28 to the main body 25 via the cylinder mount plate 31. Air inlet 32 can also be clearly seen.

FIG. 2D shows how the mounting plate 31 attaches the cylinder 28 to the main body 25 in more detail. An end cap 84 is secured to the top of the cylinder 28 with the shaft of piston 27 extending up through the end cap 84. The plate 31 is inserted over the end cap 84 and secured to it by a nut 87 which is threaded onto the end cap 84. One or more screws 86 attach the mounting plate 31 to the main body 25, and thereby, rigidly attach cylinder 28 to main body 25. Note that a second (optional) air inlet port 90 is formed in end cap 84. End cap 84 may or may not include this optional inlet port 90. As is explained in more detail below, FIG. 3A shows an embodiment of the invention wherein cylinder 28 has only one air input port 32, and FIG. 3D shows an embodiment where cylinder 28 has the additional air inlet port 90.

The piston and cylinder are coupled to a compressed air supply at air inlet connection 32 (and optionally air inlet port 90). The air supply can be controlled using suitable valves connected to control electronics. Suitable piston and cylinder assemblies and suitable electronically controlled valves are available from Bosch Rexroth, of 15 Cromwell Road, St. Neots, PE19 2ES, United Kingdom. Alternative suppliers are Festo Ltd of Caswell Road, Brackmills, Northampton, NN4 7PY, United Kingdom and Pneumax Ltd., Unit 7/8, Venture Industrial Park, Gosport, PO13 0BA, United Kingdom.

Figure 3A:
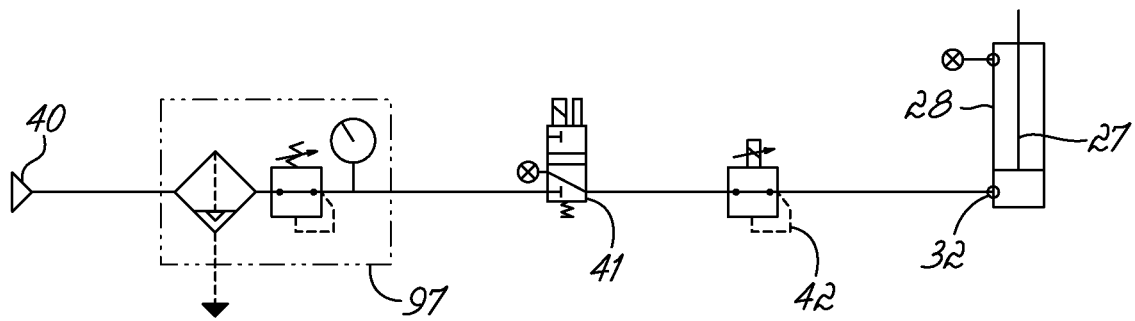
FIG. 3A is a schematic illustration of the pneumatic control system for the piston and cylinder shown in FIG. 2C.

FIG. 3A is a schematic illustration of the control system for the pneumatic piston and cylinder. The piston 27 moves axially within cylinder 28. Air is both supplied to the cylinder and escapes from the cylinder through port 32. Port 32 is coupled to a pneumatic control system comprising a compressed air supply 40, regulator 97, a supply valve 41 and exhaust valve 42. Supply valve 41 selectively connects the compressed air supply to the port 32, to thereby drive the piston 27 upwardly within the cylinder 28 to provide the desired biasing force to the nut 34 by setting the desired air pressure at a regulator 97. Exhaust valve 42 selectively vents air in the cylinder 28 to the environment, thereby removing any biasing force supplied by the piston 27. When the interior of the cylinder is in open fluid communication with the environment via the exhaust valve 42, the piston 27 is free to move within the cylinder 28. The supply valve 41, exhaust valve 42 and regulator 97 are connected to control electronics 56, described with reference to FIG. 5.

Figure 4:
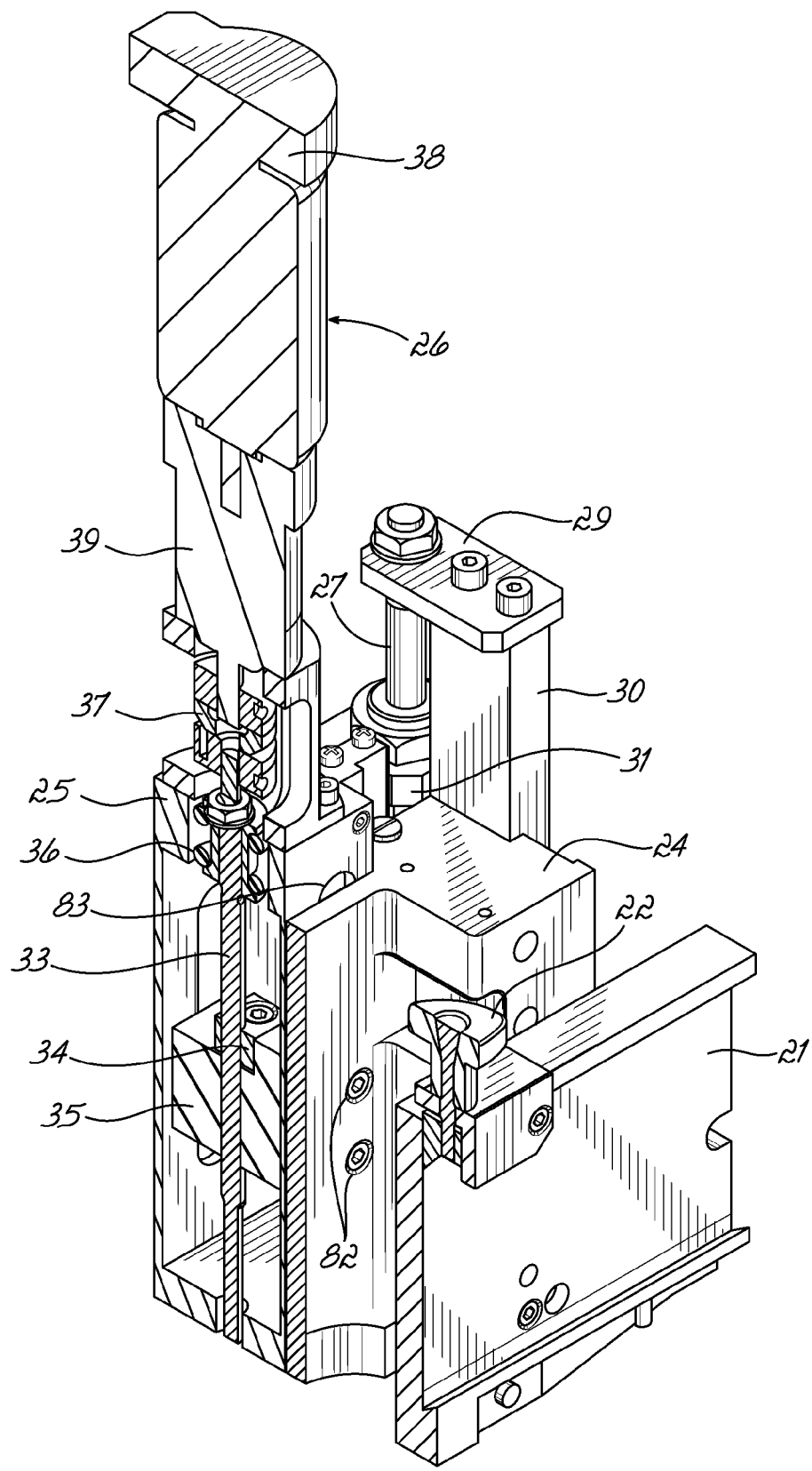
FIG. 4 is a perspective, cut away view of the test tool mount and drive illustrated in FIG. 2A-2C.

In FIG. 4, the arrangement of screw 33 and nut 34 can be clearly seen. The nut 34 is rigidly coupled to moving block 24 via nut block 35, while the screw 33 is supported by bearings 36 on the main body 25 of the device, and allowed to rotate about its axis. Nut block 35 is rigidly fixed to moving block 24 using screws 82 that can travel along a slot 83 in the main body 25. The top end of slot 83 is shown in FIG. 4. A servo motor 26 is fixed to the main body 25 and is coupled to the screw 33 via a coupling 37, to rotate the screw, thereby moving the nut 34 up and down the length of the screw 33. The motor assembly fixed to the main body 25 comprises the motor 26, an encoder 38 and a gearbox 39, available from Trident Engineering Ltd., Trident House, King Street Lane, Winnersh, Wokingham, Berkshire, RG41 5AS, United Kingdom. Alternatively, a direct drive motor and encoder assembly may be used, without a gearbox. An assembly of this type is available from Maxon Motors Ltd., Maxon House, Hogwood Lane, Finchampstead, Berkshire, RG40 4QW, United Kingdom. Accurate control of the motor 26 using suitable control electronics provides accurate control of the vertical position of the cartridge mount plate 21 and hence the test tool 10.

During a shear test, such as is described in U.S. Pat. No. 6,078,387, where the tool 10 is normally shearing a solder ball deposit off of a substrate, the bond under test exerts an upward force on the test tool. In order to ensure that the tip of the test tool remains accurately positioned during a test and that the test is repeatable, an upward biasing force is applied by the piston 27 on the moving body 24 which can be set at the desired level and maintained consistently. As previously mentioned, the same upward biasing force is used during a push test. This upward biasing force eliminates backlash between the screw 33 and nut 34 described above.

In a pull test, such as is described in U.S. Pat. No. 6,301,971, a wire is pulled off a bond that attaches the wire to the substrate. The wire being pulled exerts a downward force on the test tool 10 during the test. In this case, the tip of the test tool would be a hook which hooks under the wire. To ensure that any backlash problems are eliminated, the piston 27 and cylinder 28 can be operated to apply a downward biasing force on the nut 34. However, instead of applying a downward biasing force using the piston 27, the weight of the vertically moving components of the system associated with test tool 10, as described above, may be enough to eliminate any backlash. Therefore, in pull tests, one option with the present invention is to turn off the air pressure to the cylinder 28 at valve 41, open the exhaust valve 42 to remove the air pressure below the piston head of piston 27 and allow the piston 27 to move freely in the cylinder 28. As mentioned above, this option of allowing the weight of the moving components to provide the necessary backlash control during pull tests was not possible with the prior art machines which utilized a spring that constantly provided an upward biasing force on the nut 34.

Figure 3B:
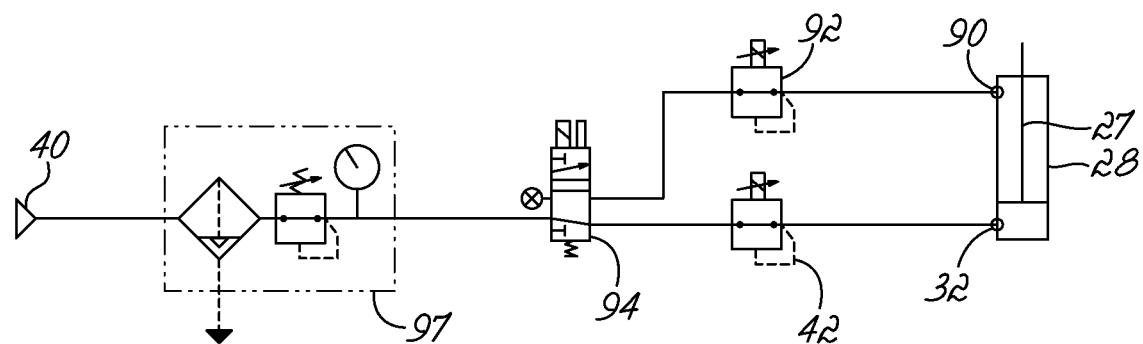
FIG. 3B is a schematic illustration of the pneumatic control system for the piston and cylinder shown in FIG. 2D.

FIG. 3B shows the alternate system wherein the weight of the vertically moving elements is not sufficient to control backlash. In this case, an additional air inlet port 90 is provided at the top of the cylinder 28 so that air pressure, set to the desired level at regulator 97, can be applied to the top side of the piston head of piston 27. When a downward bias is to be applied to the nut 34 using the piston 27, exhaust valve 42 is opened, exhaust valve 92 is closed, regulator 97 is set at the desired air pressure level and control valve 94 directs pressurized air through inlet 90 into chamber 28 to apply the desired downward biasing force to piston 27 and nut 34. When an upward bias is to be applied to nut 34 using the piston 27, exhaust valve 42 is closed, exhaust valve 92 is opened, the air pressure is set to the desired level at regulator 97 and control valve 94 directs pressurized air through inlet 32 into chamber 28 to apply the desired upward biasing force to piston 27 and nut block 35.

Figure 5A:
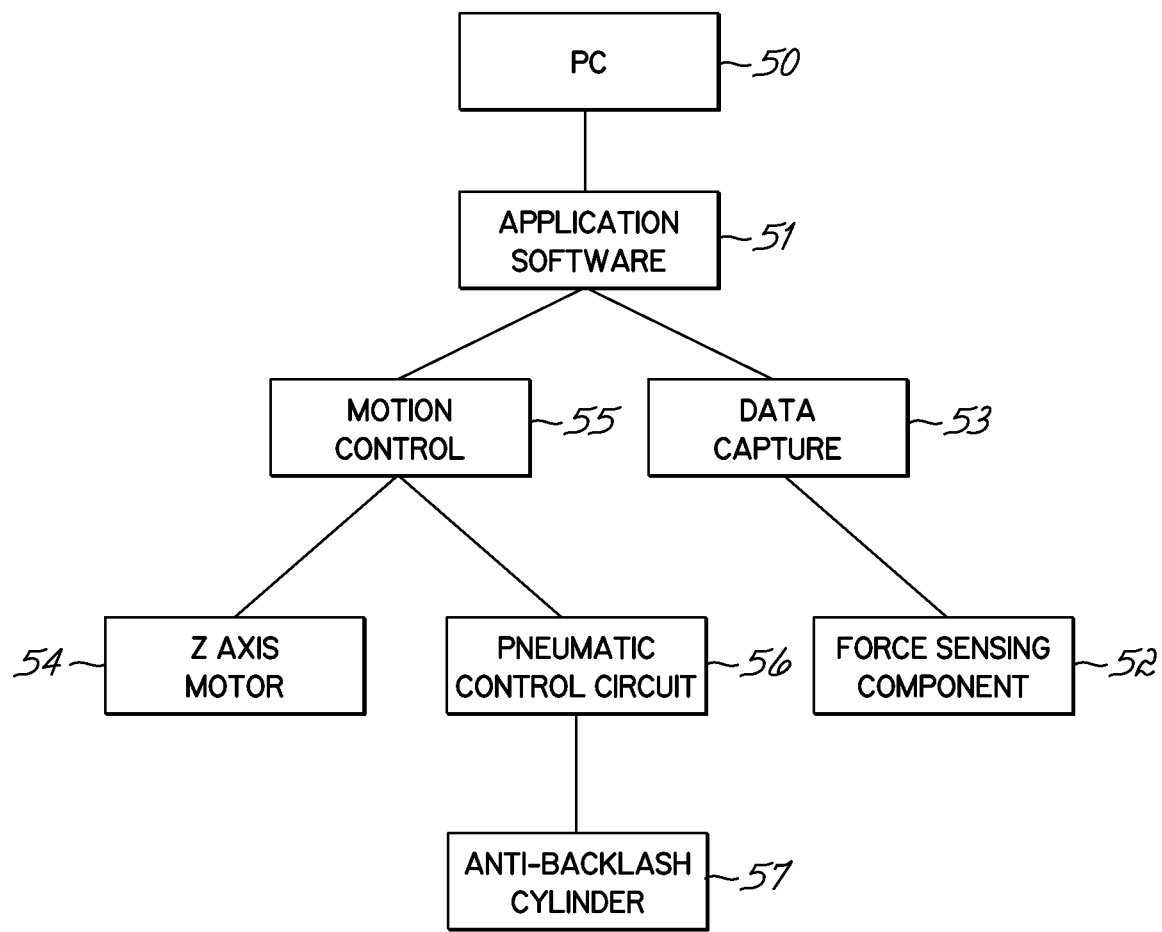
FIG. 5A is a schematic diagram illustrating the control elements of a system in accordance with the present invention.
Figure 5B:
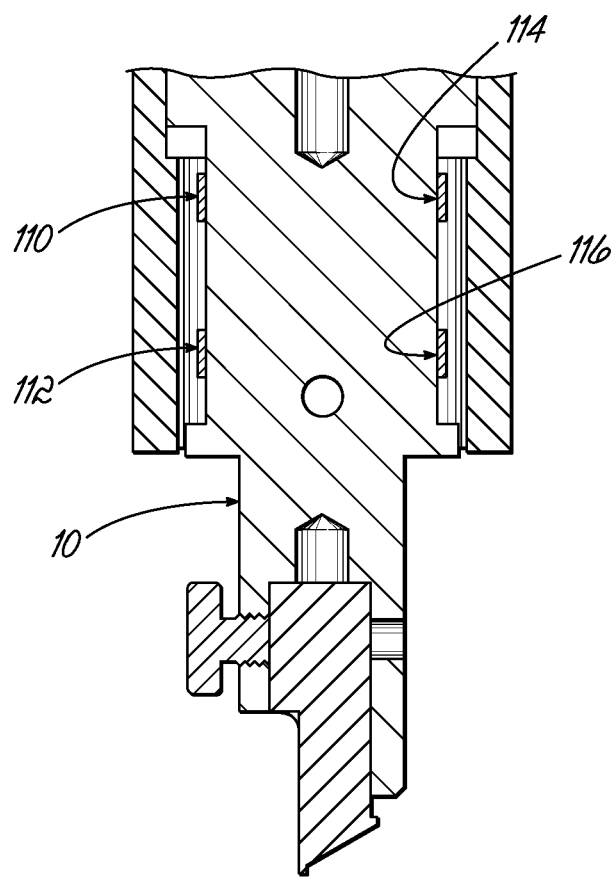
FIG. 5B is cross-sectional view showing the strain gauges attached to the test tool.

FIG. 5A illustrates the control elements of a system in accordance with the present invention. The system is controlled by application software 51 running on a personal computer 50, which includes a user interface. The test tool 10 typically includes force sensing components 52, such as a piezoelectric crystal or a strain gauge. FIG. 5B shows one example of a test tool 10 which has four strain gauges 110, 112, 114, and 116 mounted thereon. Since this test tool is used for shear tests, the strain gauges 110-116 will become distorted as the test tool flexes while shearing a ball deposit off a substrate. Using well-known technology, the physical distortion of the strain gauges will produce electric signals that are processed by known circuitry to produce an indication of the force required to shear the ball deposit off the substrate. As mentioned previously, by accurately controlling the standoff distance of the test tool above the substrate during a shear test using the anti-backlash solution of the present invention, electric signals produced by the strain gauges more accurately, and more repeatedly, measure the force required to shear the ball deposit off the substrate. U.S. Pat. No. 6,301,971 describes another example wherein, in a pull test device, the strain gauges are mounted on the cantilever arms that support the test tool. Here again, accurate positioning of the test tool using the anti-backlash solution of the present invention improves the accuracy and repeatability of the force measurements produced. WO 2006/016136 A2 describes yet another example wherein a piezoelectric crystal is mounted on the test tool to measure shear forces. Again, accurate control of the position of the test tool, using the present invention, improves test accuracy and repeatability.

Regardless of whether strain gauges or a piezoelectric crystal is used as the force sensing component 52, the electrical output from this component 52 is processed by the data capture electronics 53 in FIG. 5A to detect the force applied to the test tool during a test procedure. The data capture electronics 53 communicate with the application software 51. The application software 51 also controls the movement and positioning of the test tool 10. In FIG. 5A, only the Z axis motor 54 for driving the screw 33 shown in FIG. 4 is shown. However, motion control electronics 55 would also control the motor moving the stage table 13. The valves 41, 42, 92 and 94, and regulator 97, of FIGS. 3A and 3B comprise the pneumatic control circuit 56 in FIG. 5A. These valves and regulator are operated to apply the desired upward or downward biasing force to the anti-backlash piston 27 within cylinder 28, or no biasing force, as described above. The piston 27 and cylinder 28 are referred to as the antibacklash component 57 in FIG. 5A.

The personal computer 50 is connected to the keyboard, joysticks and display shown in FIG. 1 to allow for user configuration and control.

Figure 6A:
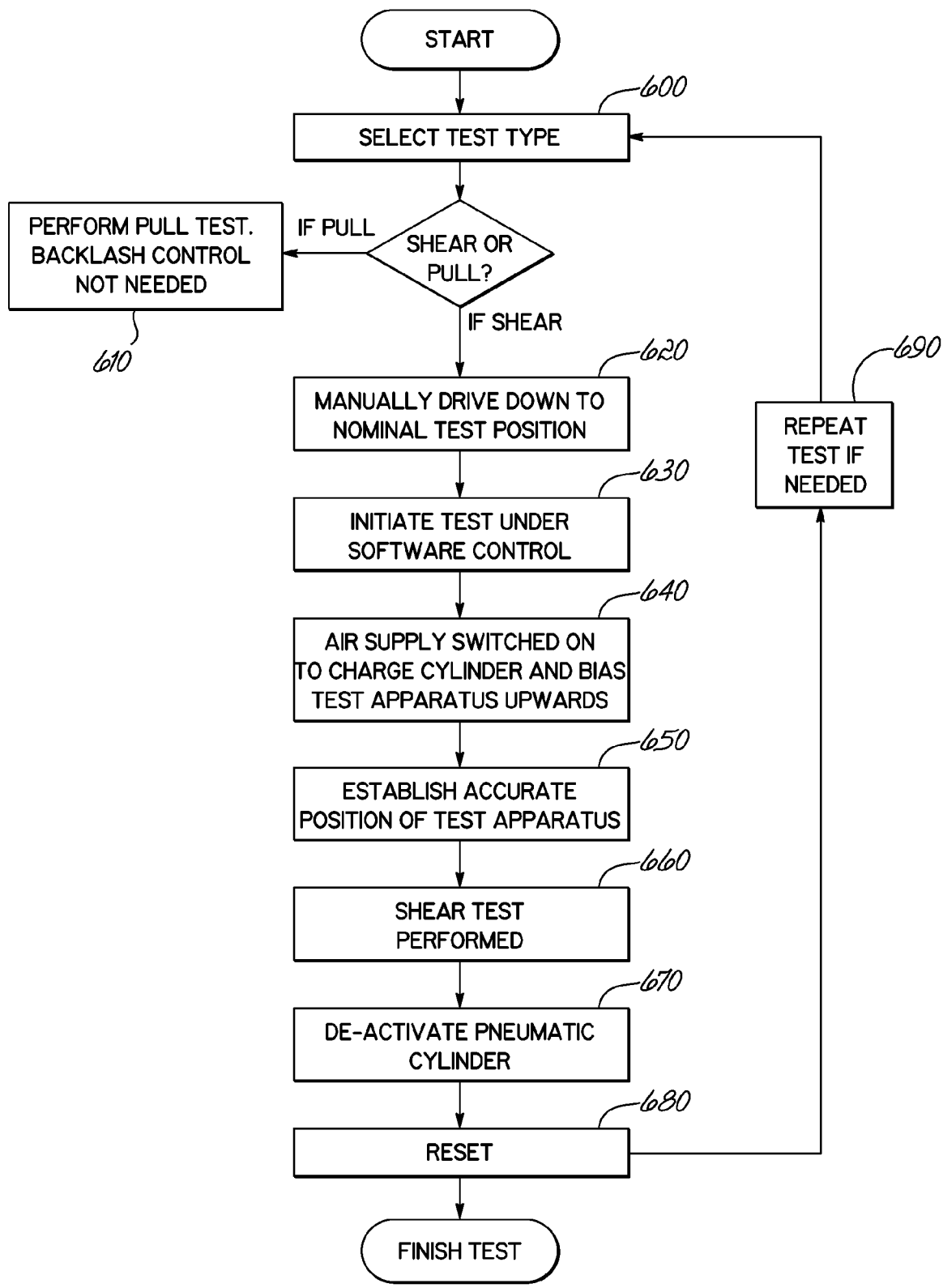
FIG. 6A is a flow diagram illustrating steps performed by an apparatus in accordance with the present invention during a bond test procedure.
Figure 6B:
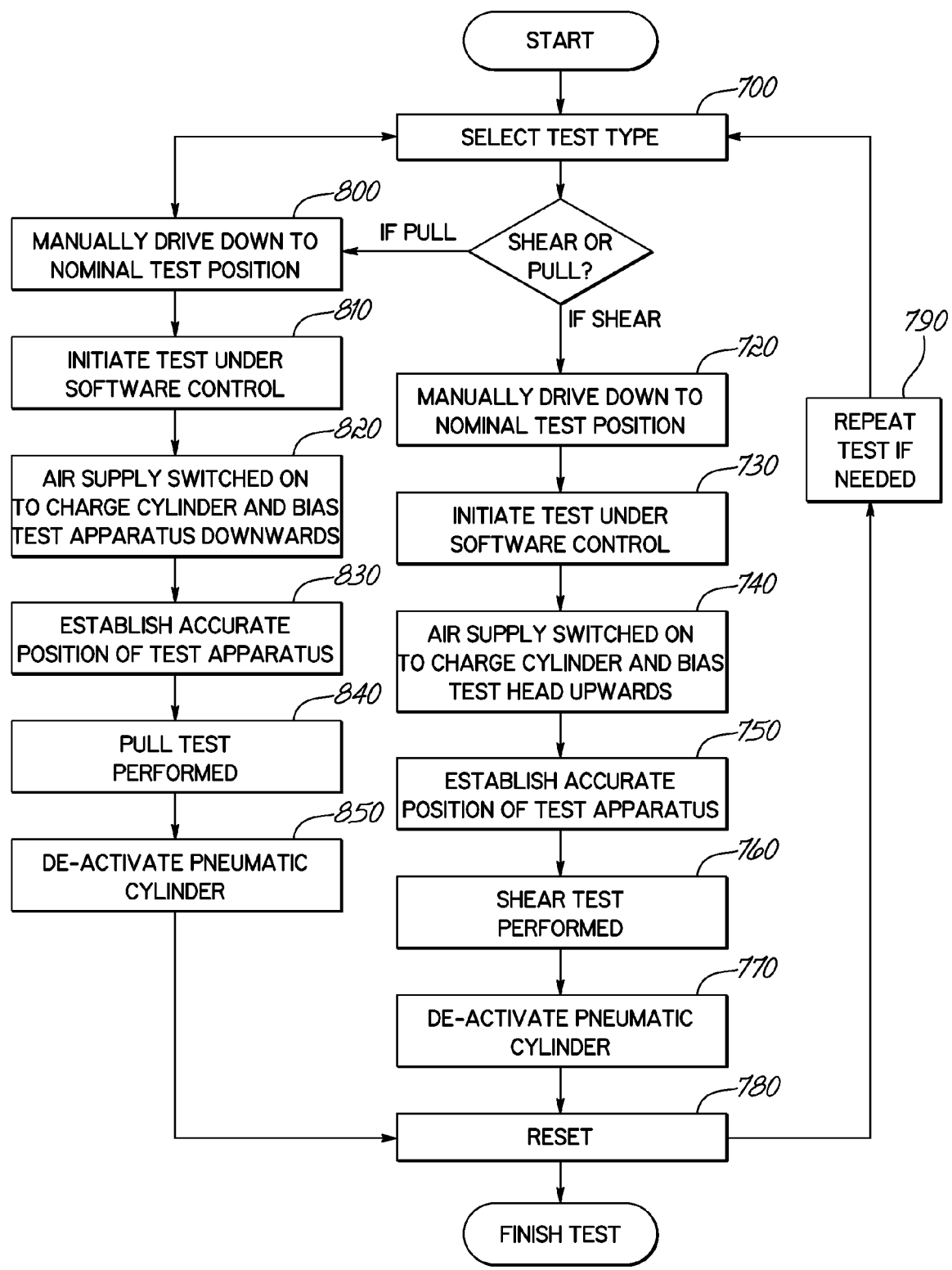
FIG. 6B is a flow diagram illustrating steps performed by an apparatus in accordance with an alternative embodiment of the present invention during a bond test procedure.

FIGS. 6A and 6B show the method steps that the system described in above goes through in performing a shear, push or pull test.

With reference to FIG. 6A, which describes the system as operated using the pneumatic control system of FIG. 3A, in the first stage 600, the test type is selected using a user interface, such as the keyboard shown in FIG. 1.

If the test is a pull test, the backlash control cylinder is not required in this embodiment and is not activated. The backlash is eliminated by the weight of the vertically moving components of the system biasing the nut into a downward position as described above. This is shown as step 610. In this situation, the exhaust valve 42 is open.

However, if a push or shear test is to be performed, at step 620, the test tool 10 is driven into the desired test position, adjacent a bond to be tested. Once the test tool has been correctly positioned, an automated test procedure can be initiated under software control, via a suitable user interface such as the keyboard, shown as step 630. The first step in the automated test procedure is that pressurized air, at the pressure set at regulator 97, is supplied to the anti-backlash cylinder 28 under the piston head of piston 27 so that the piston 27 operates to bias the nut 34 into an upward position with the desired biasing force. This is shown as step 640. Backlash is thereby removed from the system. After step 640 has been performed, the test tool is raised from the surface of the substrate to be tested by a predetermined step off distance in step 650, and the shear test is then performed in step 660, with a constant biasing force maintained throughout the test. Once the test is complete, air supply valve 41 is closed and exhaust valve 42 is opened to remove air pressure from under the piston head of piston 27 in step 670. The system is reset in step 680. A new test can then be performed as indicated in block 690.

With reference to FIG. 6B, which describes the system when operated with the pneumatic control system of FIG. 3B, many of the method steps are the same as described above with reference to FIG. 6A, however, some steps are different.

In the first step 700, the test type is selected using a user interface, such as the keyboard shown in FIG. 1.

If the test is a shear or push test, at step 720, the test tool 10 is driven into the desired test position, adjacent a bond to be tested. Once the test tool has been correctly positioned, an automated test procedure can be initiated under software control, via a suitable user interface such as the keyboard, shown as step 730. The first step in the automated test procedure is that pressurized air, at the pressure set at regulator 97, is supplied to the anti-backlash cylinder 28 under the piston head of piston 27 through inlet 32 so that the piston 27 operates to bias the nut 34 into an upward position with the desired biasing force. During this step, vent valve 92 is open. These actions are indicated at step 740. Backlash is thereby removed from the system. After step 740 has been performed, the test tool is raised from the surface of the substrate to be tested by a predetermined step off distance in step 750, and the shear test is then performed in step 760, with a constant biasing force maintained throughout the test. Once the test is complete, air supply valve 41 is closed and exhaust valve 42 is opened to remove air pressure from under the piston head of piston 27 in step 770. The system is reset in step 780. A new test can then be performed as indicated in block 790.

If a pull test is selected at step 700, at step 800 the test tool 10 is driven into the desired test position, adjacent a bond to be tested. Once the test tool has been correctly positioned, an automated test procedure can be initiated under software control, via a suitable user interface such as the keyboard, shown as step 810. The first step in the automated test procedure is that pressurized air, at the pressure set at regulator 97, is supplied to the anti-backlash cylinder 28 above the piston head of piston 27 through inlet 32 so that the piston 27 operates to bias the nut 34 into an downward position with the desired biasing force. Vent valve 42 is open. These actions are indicated at step 820. Backlash is thereby removed from the system. After step 820 has been performed, the test tool is raised from the surface of the substrate to be tested by a predetermined step off distance in step 830, and the pull test is then performed in step 840, with a constant biasing force on nut 34 maintained throughout the test. Once the test is complete, air supply valve 41 is closed and exhaust valve 92 is opened to remove air pressure from above the piston head of piston 27 in step 850. The system is reset in step 780. A new test can then be performed as indicated in block 790.

In the foregoing description, the means for removing backlash is a pneumatically operated piston and cylinder. However other means of biasing the nut relative to the screw are possible, such as a compression spring that can be mechanically or manually moved into and out of engagement with the test tool mount or the main body so that the biasing can be switched on and off.

The invention claimed is:

1. A testing apparatus for testing the strength of a material connection to a substrate, comprising:
   a main body,
   a test tool mount for holding a test tool,
   an axial drive mechanism, the drive mechanism coupling the test tool mount to the main body and allowing for relative movement between the test tool mount and the main body in an axial direction, and
   a biasing element, coupled between the main body and the test tool mount, that, in operation, biases the test tool mount relative to the main body in an axial direction, wherein the biasing element is switchable by a user between a first state in which the test tool mount is biased either toward or away from the substrate and another state in which the biasing element provides one of: no biasing force to the test tool mount toward or away from the substrate, or a biasing force in a direction opposite to the direction of bias applied in the first state.

2. A testing apparatus according to claim 1, wherein the biasing element comprises a pneumatically operated piston and cylinder.

3. A testing apparatus according to claim 2, wherein the piston is coupled for movement with the test tool mount and the cylinder is fixed in position relative to the main body.

4. A testing apparatus according to claim 2, wherein the axial drive mechanism comprises a screw and nut assembly, wherein the piston is coupled for movement with the nut and the cylinder is fixed in position relative to the screw.

5. A testing apparatus according to claim 1, further comprising a controller connected to a user interface, the controller and user interface being configured to allow a user to select a type of test, and wherein the controller is connected to the biasing element and controls switching of the biasing element.

6. A testing apparatus according to claim 1 wherein the biasing element provides a biasing force which can be set at different force levels.

7. A testing apparatus according to claim 6 wherein the biasing element comprises a pneumatically operated piston and cylinder and wherein the cylinder can be charged with different air pressure settings to provide different biasing force levels.

8. A testing apparatus according to claim 1, wherein the biasing element provides a biasing force which can be maintained as a constant force as the test mount moves axially relative to the main body.

9. A testing apparatus according to claim 1, wherein in the first state an upward bias is applied by the biasing element to the test tool mount.

10. A testing apparatus according to claim 1, further comprising a controller connected to a user interface, the controller and user interface being configured to allow a user to select a type of test, and wherein the controller is connected to the biasing element and controls switching of the biasing element, and wherein when a user selects a type of test, a bias is applied by the biasing element to the test tool mount in the same direction as the force resulting from the type of test selected.

11. A method of testing the strength of a material connection to a substrate by using a testing device comprising a test tool coupled to a main body, comprising the steps of:
  selecting a test;
  applying a biasing force on the test tool in a first direction;
  positioning the test tool relative to the material;
  providing relative movement between the test tool and the substrate in a manner that results in a force being applied by the material to the test tool in the first direction; and
  recording the force applied to the test tool by the material.

12. A method according to claim 11, wherein the step of applying a biasing force comprises operating a pneumatic cylinder and piston coupled between the test tool and the main body.

13. A method according to claim 11, further comprising the step of initially positioning the test tool relative to the material prior to applying a biasing force on the test tool, and more accurately positioning the test tool relative to the material subsequent to applying a biasing force on the test tool.

* * * * *